(12) United States Patent
Bartish et al.

(10) Patent No.: US 7,235,082 B2
(45) Date of Patent: Jun. 26, 2007

(54) DEVICE FOR INSERTION OF IMPLANTS

(75) Inventors: Charles Bartish, East Providence, RI (US); Jeff Brousseau, Barrington, RI (US); David Konieczynski, Needham, MA (US); Stephen Connolly, Sharon, MA (US)

(73) Assignee: DePuy Spine, Inc., Raynham, MA (US)

( * ) Notice: Subject to any disclaimer, the term of this patent is extended or adjusted under 35 U.S.C. 154(b) by 347 days.

(21) Appl. No.: 10/639,782

(22) Filed: Aug. 12, 2003

(65) Prior Publication Data

US 2005/0038431 A1 Feb. 17, 2005

(51) Int. Cl.
*A61B 17/88* (2006.01)

(52) U.S. Cl. .................................................. 606/99

(58) Field of Classification Search ............... 294/19.4, 294/19.1; 606/100, 61, 99; 623/16.11–17.16
See application file for complete search history.

(56) References Cited

U.S. PATENT DOCUMENTS

| | | | | |
|---|---|---|---|---|
| 1,591,528 | A | * | 7/1926 | Giefers ........................ 131/259 |
| 3,574,381 | A | * | 4/1971 | Ocheltree et al. .......... 294/19.1 |
| 4,239,045 | A | | 12/1980 | Schlein |
| 4,677,972 | A | * | 7/1987 | Tornier ......................... 606/53 |
| 5,122,130 | A | | 6/1992 | Keller |
| 5,324,293 | A | * | 6/1994 | Rehmann ..................... 606/85 |
| 5,443,514 | A | | 8/1995 | Steffee |
| 5,522,899 | A | | 6/1996 | Michelson |
| 5,540,697 | A | * | 7/1996 | Rehmann et al. ............. 606/91 |
| 5,697,889 | A | * | 12/1997 | Slotman et al. ............. 600/204 |
| 5,716,415 | A | | 2/1998 | Steffee |
| 5,766,252 | A | | 6/1998 | Henry et al. |
| 5,776,199 | A | * | 7/1998 | Michelson ............... 623/17.16 |
| 5,782,830 | A | * | 7/1998 | Farris .......................... 606/61 |
| 5,888,224 | A | | 3/1999 | Beckers et al. |
| 5,989,289 | A | | 11/1999 | Coates et al. |
| 6,080,158 | A | | 6/2000 | Lin |
| 6,224,607 | B1 | | 5/2001 | Michelson |
| 6,319,257 | B1 | * | 11/2001 | Carignan et al. ............. 606/99 |
| 6,425,920 | B1 | | 7/2002 | Hamada |
| 6,443,987 | B1 | | 9/2002 | Bryan |
| 6,464,727 | B1 | | 10/2002 | Sharkey et al. |

(Continued)

FOREIGN PATENT DOCUMENTS

EP 1 224 916 A2 7/2002

*Primary Examiner*—Eduardo C. Robert
*Assistant Examiner*—Richard Shaffer
(74) *Attorney, Agent, or Firm*—Nutter, McClennen & Fish LLP

(57) ABSTRACT

A device and method, which can be used for insertion of surgical implants, are provided in which the device includes a shaft having a proximal end and a distal end, and at least one moveable element. In a particular embodiment, the moveable element is disposed within a conduit defined by the shaft. The moveable element includes a leg extending through the conduit and a foot at an end of the leg proximal to the distal end of the shaft. The element is moveable relative to the shaft between a first position, wherein the foot extends beyond the distal end, and a second position, wherein the foot is substantially adjacent to the distal end. The device can further include a surgical implant that can be removably attached to the distal end.

24 Claims, 8 Drawing Sheets

U.S. PATENT DOCUMENTS

| | | |
|---|---|---|
| 6,478,823 B1 | 11/2002 | Michelson |
| 6,530,955 B2 | 3/2003 | Boyle et al. |
| 6,582,432 B1 | 6/2003 | Michelson |
| 2002/0040243 A1* | 4/2002 | Attali et al. ............. 623/17.16 |
| 2003/0114854 A1 | 6/2003 | Pavlov et al. |

* cited by examiner

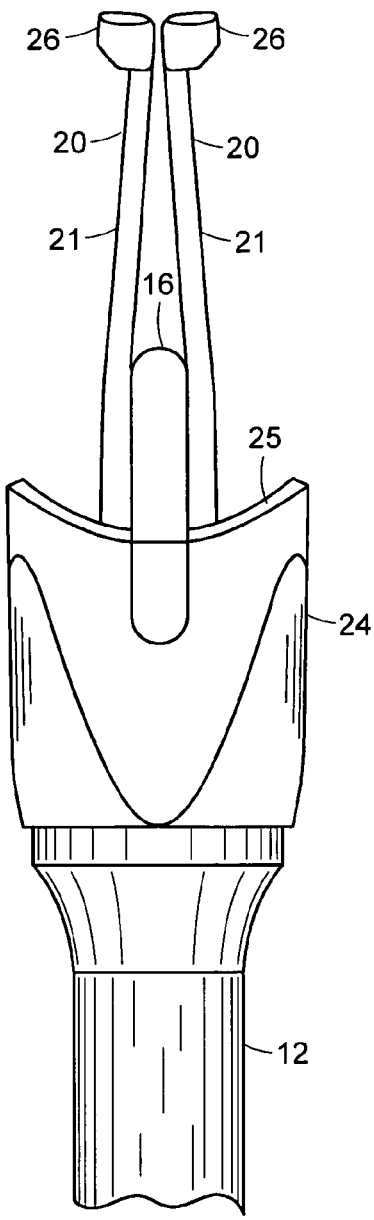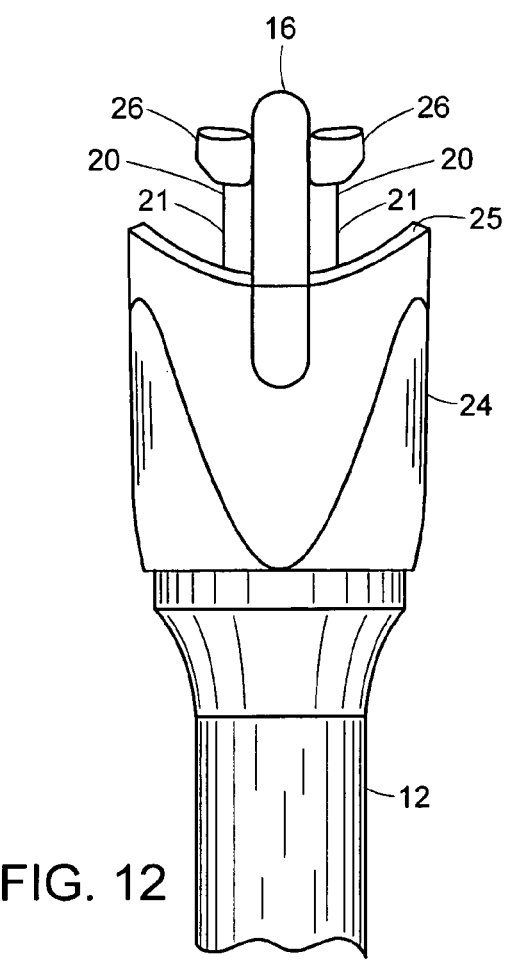
FIG. 11
FIG. 12

DEVICE FOR INSERTION OF IMPLANTS

BACKGROUND OF THE INVENTION

Implants can be used, for example, to fuse spinal vertebrae to alleviate pain and discomfort associated with injured intervertebral disks. Unfortunately, insertion of implants can be challenging. Often the device for insertion of implants, which can be referred to as an inserter, is required to mechanically attach to the implant and provide rotational control. This provides the surgeon with the ability to control the implant and achieve the desired positioning within the patient during insertion of the implant. Once the implant is positioned within the patient, the inserter is disengaged from the implant.

One prior art system utilizes a threaded insertion mechanism that pulls the implant into an anti-rotation feature. However, this approach does not work well with thinner wall implants that may not have enough material to support threads or there are too few threads to prevent stripping. This can also be problematic for different materials, such as polyetheretherketone (PEEK) or carbon fiber reinforced polymers (CFRP). These particular materials have the advantage of radiolucency, but tend to be brittle or lack necessary strength to support threads.

Other prior art systems grab or pinch the implant on its sides. This approach works well for implants that do not have enough wall thickness to support threads. Also, this approach works well for certain materials, such as allograft, that cannot be tapped. Typically, these inserters require a larger entrance in the patient than would be required to receive an implant. The larger entrance is needed to accommodate the pinching mechanism.

SUMMARY OF THE INVENTION

A device, which can be used for insertion of surgical implants, is provided that includes a shaft having a proximal end and a distal end, and at least one moveable element. In a particular embodiment, the moveable element is disposed within a conduit defined by the shaft. The moveable element includes a leg extending through the conduit and a foot at an end of the leg proximal to the distal end of the shaft. The element is moveable relative to the shaft between a first position, wherein the foot extends beyond the distal end, and a second position, wherein the foot is substantially adjacent to the distal end.

The device can further include a surgical implant, which defines an opening having a diameter greater than a diameter of the foot, and less than the sum of the diameter of the foot and a diameter of the distal end of the shaft at a cross section of the foot and the distal end when the element is in the second position, whereby the foot can be directed through the opening when the element is in the first position. The surgical implant can be fixed at the distal end when the leg and distal end extend through the opening and the moveable element is in the second position.

The device can further include at least two moveable elements. In one embodiment, the opening of the surgical implant has a diameter greater than a sum of diameters of the feet of the moveable elements, and less than the sum of the diameters of the feet of the elements and the distal end of the shaft at a cross section of the feet and the distal end when the elements are in the second position, whereby the surgical implant is fixed at the distal end when the legs and distal end extend through the opening and the moveable elements are in the second position. The moveable elements can be on opposite sides of the distal end, whereby the feet of the moveable elements extend in substantially opposite directions from the distal end when the moveable elements are in the second position. Major axes of the moveable elements are positioned at an acute angle relative to each other in one embodiment, whereby movement of the moveable elements from the first position to the second position causes the feet of the moveable elements to move away from each other.

In particular embodiments, the moveable elements can be arcuate, whereby movement of the elements from the first position to the second position distends the legs, thereby causing the feet to move away from each other.

A saddle can be located between the proximal and distal ends of the shaft. In one embodiment, the saddle generally conforms to a portion of the surgical implant and abuts the surgical implant when the moveable elements and the distal end extend through the opening and the moveable elements are in the second position. The surgical implant that conforms to the saddle at least partially supports the position of the surgical implant relative to the shaft when the moveable elements and the distal end extend through the opening and the moveable ends are in the second position. The surgical implant that conforms to the saddle can include at least one flat surface. In other embodiments, the portion of the surgical implant that conforms to the saddle includes at least two flat surfaces that intersect.

In one embodiment, the surgical implant is a vertebral cage that can be elongate and generally arcuate. The opening in the implant can be at an end of the elongate vertebral cage.

A method is also provided that includes providing a shaft having a proximal end and a distal end, the shaft defining a conduit, and providing at least one moveable element, the element including a leg extending through the conduit and a foot at an end of the leg proximal to the distal end of the shaft. The method includes moving the moveable element relative to the shaft between a first position, wherein the foot extends beyond the distal end, and a second position, wherein the foot is substantially adjacent to the distal end.

The method can further include removably attaching a surgical implant to the distal end. The surgical implant can define an opening that has a diameter greater than a diameter of the foot, and less than the sum of the diameter of the foot and a diameter of the distal end of the shaft at a cross section of the leg and distal end when the element is in the second position, whereby the foot can be directed through the opening when the element is in the first position, and whereby the surgical implant is fixed at the distal end when the leg and distal end extend through the opening and the moveable element is in the second position.

The method can also include providing at least two moveable elements, wherein the opening of the surgical implant has a diameter greater than a sum of diameters of the feet of the moveable elements and less than the sum of the diameters of the feet of the elements and the distal end, whereby the surgical implant is fixed at the distal end when the legs and distal end extend through the opening and the moveable elements are in the second position.

A method is further provided for surgically implanting an intervertebral support, comprising inserting a moveable element into an opening defined by a surgical implant, the moveable element having a leg and a foot at an end of the leg, and the opening having a diameter greater than a diameter of the foot and less than that of the foot and a diameter of the distal end of a shaft defining a conduit in which the leg of the moveable element is located. The moveable element is moved relative to the shaft from a first position when the foot extends beyond the distal end, to a second position, wherein the foot is substantially adjacent to the distal end, whereby the distal end enters the opening of the surgical implant and the foot is essentially adjacent to the distal end, thereby causing the surgical implant to be fixed to the distal end. The surgical implant is then inserted between two vertebrae of a patient. The moveable element is moved from the second position to the first position, thereby releasing the surgical implant from the shaft, and the moveable element is withdrawn from the opening of the surgical implant.

The invention has many advantages. For example, embodiments of the invention provide for insertion of implants, which can be thin walled, into a patient while minimizing the size of the incision in the patient. Additionally, improved rotational control of the implant during implantation is achieved.

BRIEF DESCRIPTION OF THE DRAWINGS

FIG. 11 is a partial side view of the distal end of the shaft illustrated in FIG. 10 illustrating moveable elements in an extended position.

FIG. 12 is a partial side view of the distal end of the shaft illustrated in FIG. 10 illustrating moveable elements in a retracted position.

DETAILED DESCRIPTION OF THE INVENTION

Figure 1:
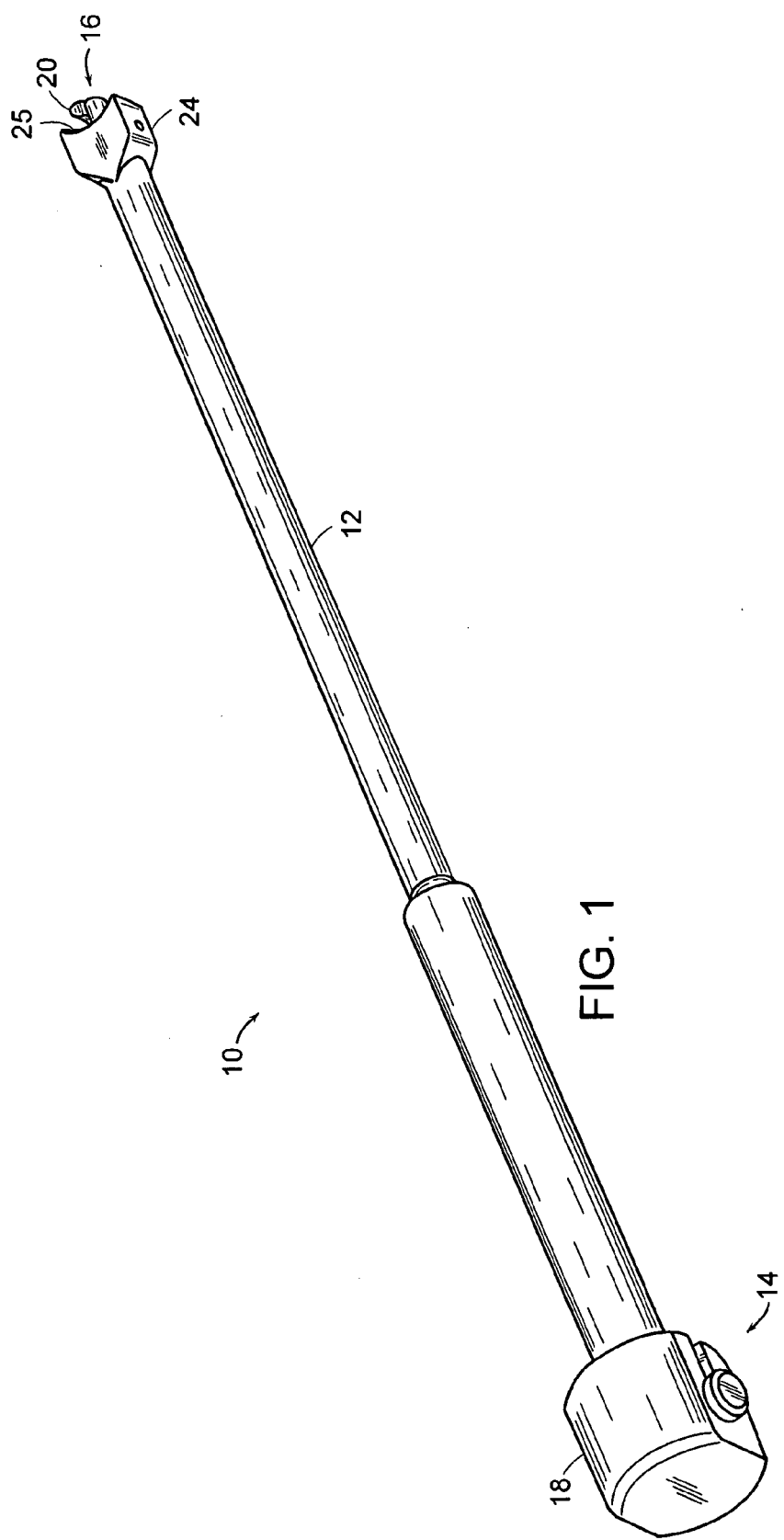
FIG. 1 is a perspective of a device for insertion of implants in accordance with an embodiment of the invention.

The foregoing and other objects, features and advantages of the invention will be apparent from the following more particular description of various embodiments of the invention, as illustrated in the accompanying drawings in which like reference characters refer to the same parts throughout the different views. The drawings are not necessarily to scale, emphasis instead being placed upon illustrating the principles of the invention.

FIG. 1 illustrates an embodiment of a device 10 for insertion of implants. In this embodiment, the device 10 includes a shaft 12 having a proximal end 14 and a distal end 16. A knob 18, positioned on the proximal end 14 of the shaft 12, is rotatable to cause a moveable element 20 to move within a conduit provided within the shaft 12. In particular embodiments, the conduit can be open on at least one side, for example, the shaft 12 can be U-shaped, C-shaped, or dovetail-shaped in cross section. In alternative embodiments, the moveable element 20 can be carried within a channel disposed along the outside of shaft 12. A hilt or saddle 24 is located between the proximal end 14 and the distal end 16 of the shaft 12. Moveable element 20 can include a leg 21 and a flange or foot 26 for removably attaching the implant 28 to the distal end 16, as will be explained below.

Figure 2:
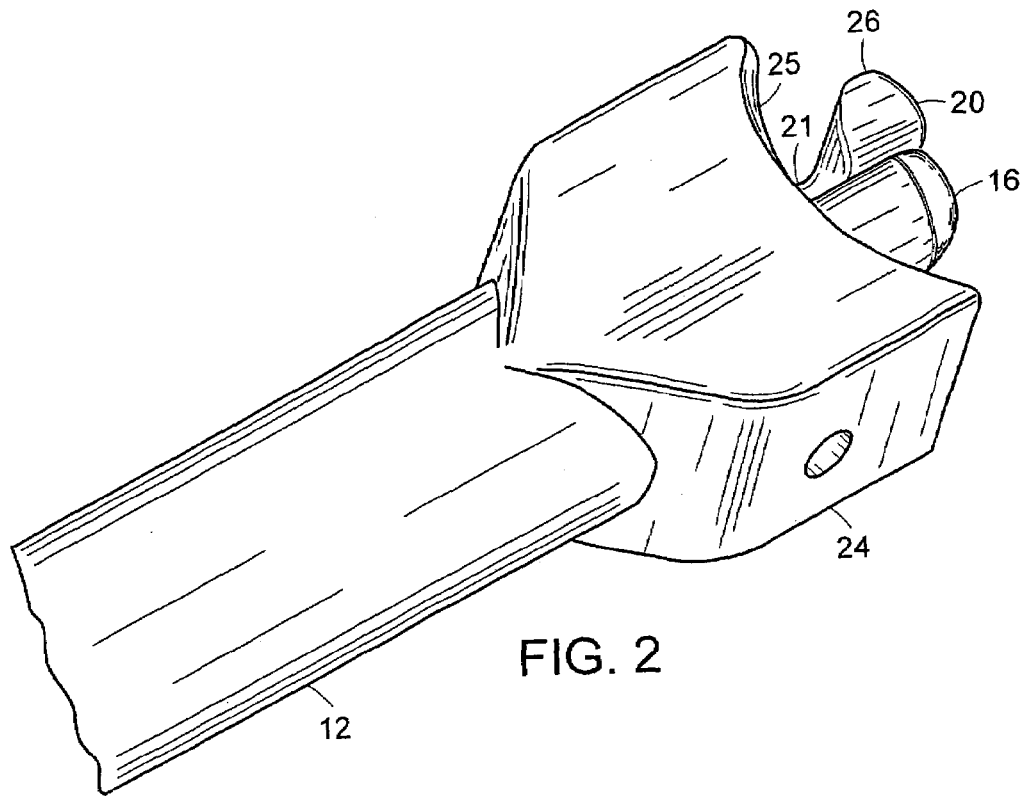
FIG. 2 is an enlarged partial perspective view of the distal end of the shaft illustrated in FIG. 1.

FIG. 2 further illustrates the distal end 16 of the shaft 12. In this embodiment, the saddle 24 is generally arcuate for mating with an implant 28 that is removably attachable to the distal end 16. Surface 25 of the saddle 24 can be knurled or otherwise provided with anti-rotation characteristics to prevent movement of the implant 28 when removably secured to the distal end 16.

Figure 3:
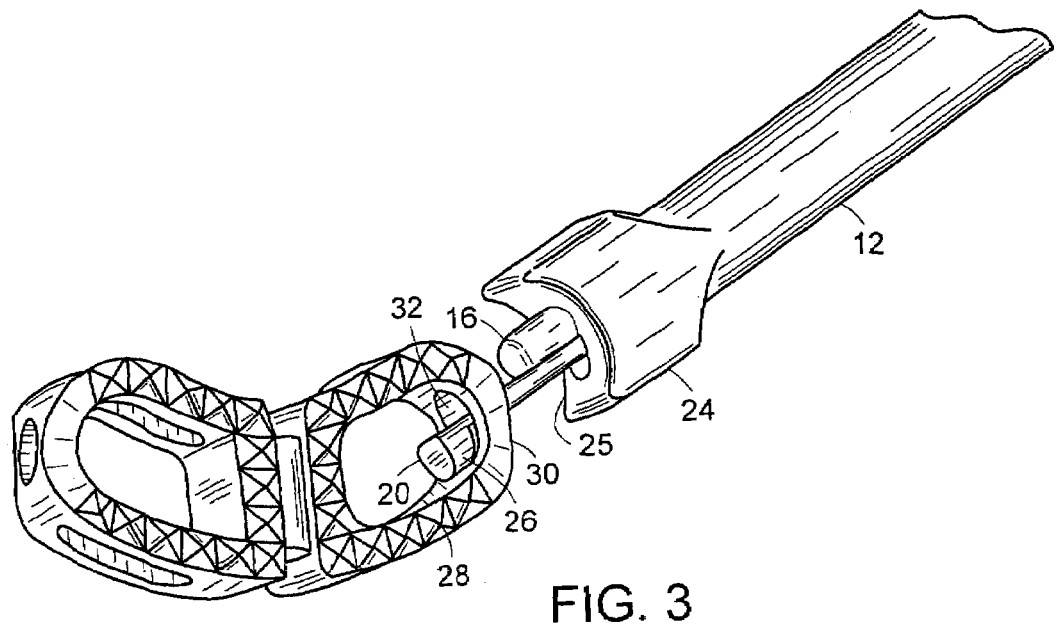
FIG. 3 is a partial perspective view of a step for attaching/detaching an implant to the device shown in FIGS. 1 and 2.
Figure 4:
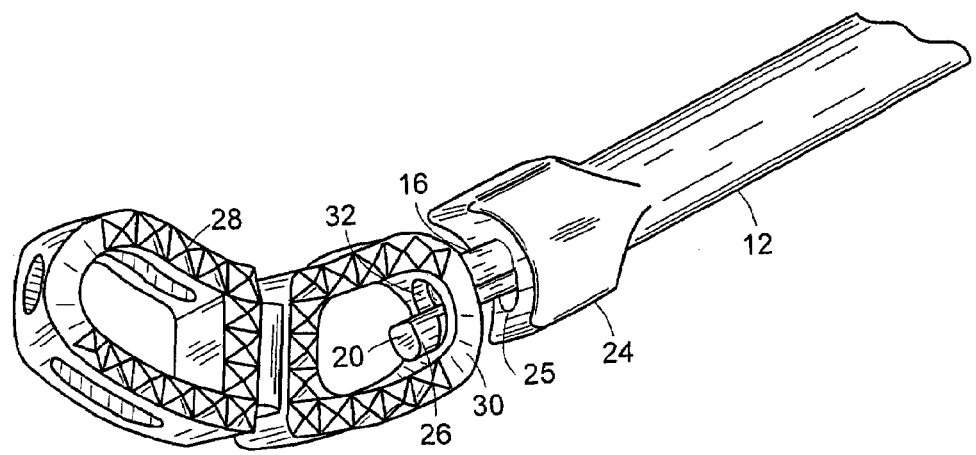
FIG. 4 is a partial perspective view of a further step for attaching/detaching an implant to the device shown in FIGS. 1 and 2.
Figure 5:
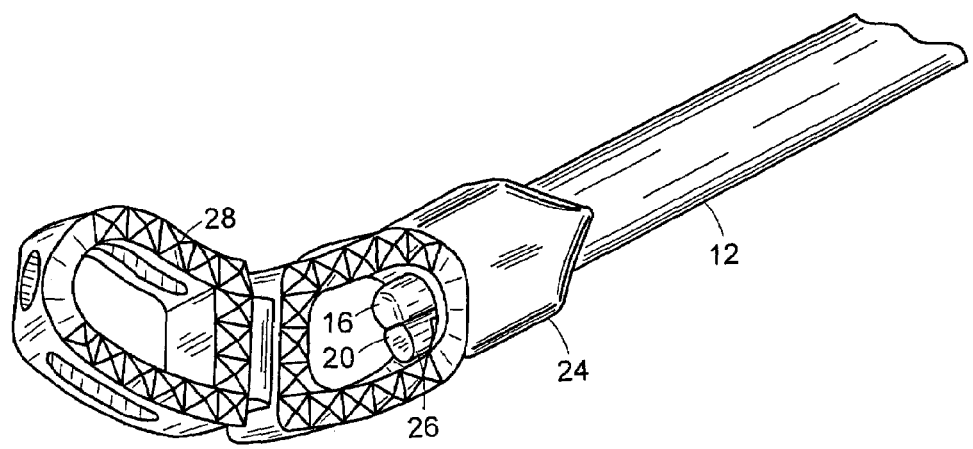
FIG. 5 is a partial perspective view of an implant removably attached to the device shown in FIGS. 1 and 2.

FIGS. 3–5 illustrate the steps for attaching the implant 28 to the distal end 16 of the shaft 12 in accordance with an embodiment of the invention. The implant 28 can include any type of surgical implant, such as an elongate, generally arcuate vertebral cage, and can include a surface 30 that is configured to mate with surface 25 of the saddle 24. As illustrated in FIG. 3, the moveable element 20 is moved to an extended or first position and inserted through an opening 32 in the implant 28. The opening 32 can include any cross-sectional shape, such as non-circular. After the foot 26 has been inserted through the opening 32, the leg 21 is moved to one side of the opening to contact the side of the opening 32 as illustrated in FIG. 4. This provides room for the distal end 16 to also be inserted into the opening 32 as the moveable element 20 is moved to a retracted position or second position in which the foot 26 is positioned substantially adjacent to the distal end 16.

With the leg 21 and distal end 16 substantially filling the opening 32, the implant 28 is removably attached to the distal end 16 of the shaft 12. The opening 32 has a diameter greater than a diameter of foot 26, which can include any cross-sectional shape, such as non-circular. As defined herein, the term diameter can refer to a straight line segment that passes through the center of a figure or element that does not have to be circular in cross-sectional shape. In one embodiment, the diameter of opening 32 is less than the sum of diameters of the foot 26 and distal end 16, which can include any cross-sectional shape, at a cross section of the foot 26 and distal end 16 when the element is in the second position, whereby foot 26 can be directed through opening 32 when element 20 is in the first position. The surgical implant 28 is fixed at distal end 16 when element 20 and distal end 16 extend through opening 32 and the moveable element 20 is in the second position. The foot 26 contacting an inside surface of the implant 28 helps transmit and distribute torque imparted from the distal end 16 to the implant 28.

Figure 6:
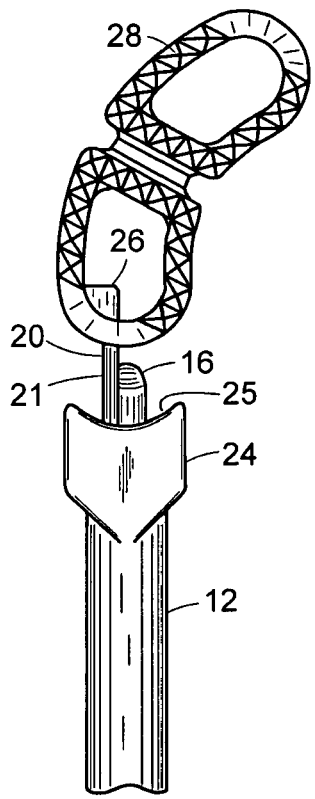
FIG. 6 is a different perspective view of the device in FIG. 3.
Figure 7:
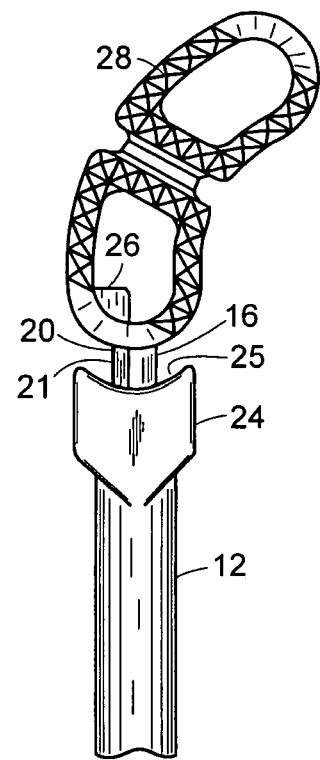
FIG. 7 is a different perspective view of the device in FIG. 4.
Figure 8:
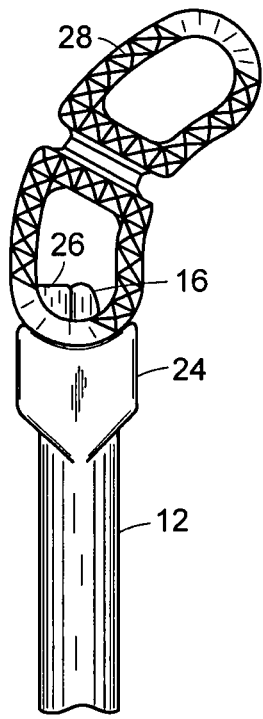
FIG. 8 is a different perspective view of the device in FIG. 5.
Figure 9:
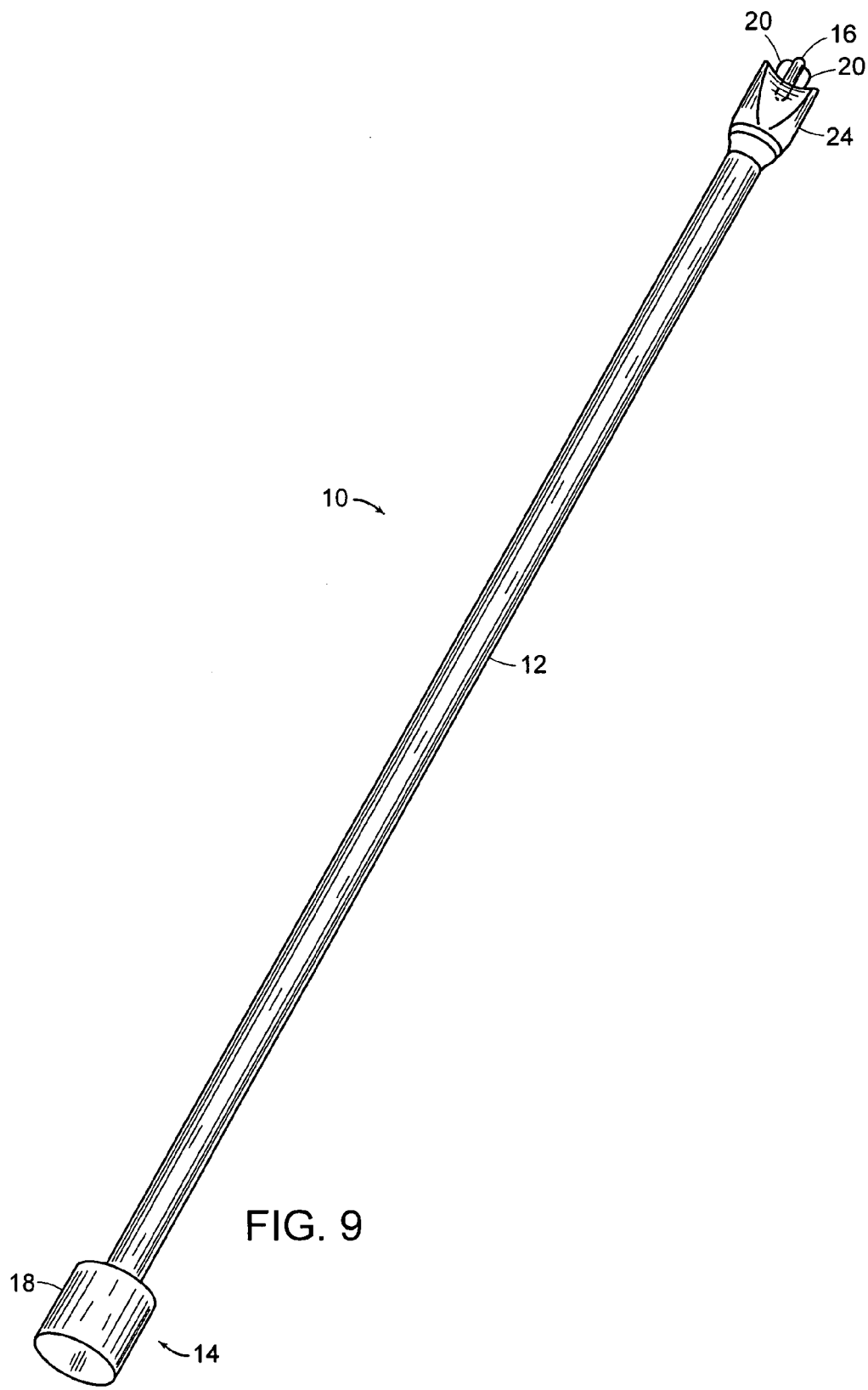
FIG. 9 is a perspective of a device for insertion of implants in accordance with another embodiment of the invention.
Figure 10:
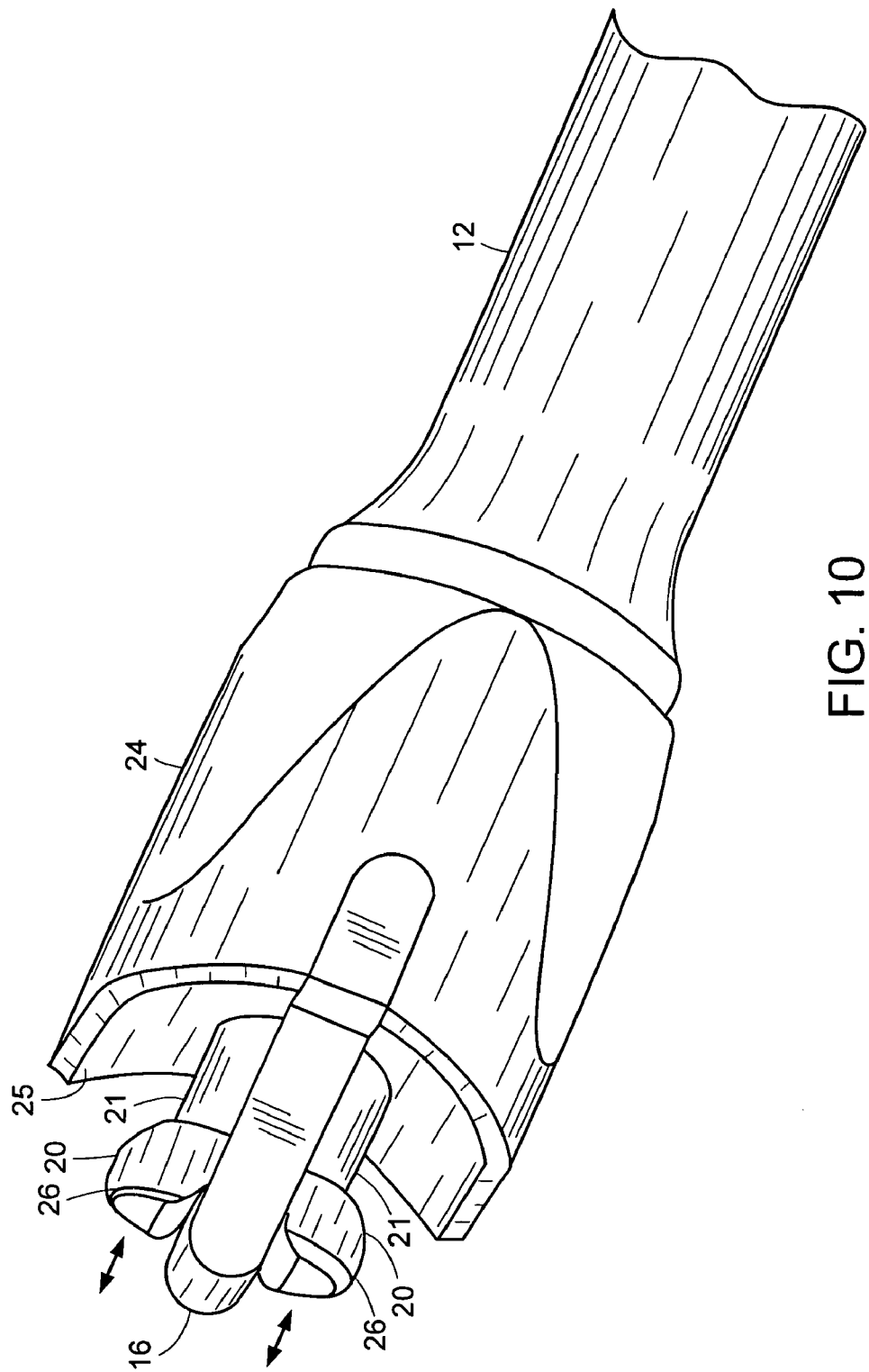
FIG. 10 is an enlarged partial perspective view of the distal end of the shaft illustrated in FIG. 9.

At least a portion of surfaces 25, 30, which can include at least one flat surface in one embodiment, mate together to at least partially support the position of the implant 28 relative to the shaft 12 when the moveable element 20 and the distal end 16 extend through the opening 32. The implant 28 can be removed by reversing the order of attachment. FIGS. 6–8 illustrate different perspectives of the views of FIGS. 3–6, respectively.

FIGS. 9–12 illustrate another embodiment of a device 10 for insertion of implants. This embodiment includes two or more moveable elements 20 moveably disposed within a conduit in the shaft 12. As shown in FIGS. 11 and 12, the moveable elements 20 are moveable between an extended position, or first position, and a second, or retracted position, respectively. In this embodiment, the moveable elements 20 are disposed on opposite sides of the distal end 16. In one embodiment, the moveable elements 20 are arcuate, whereby movement of the elements from the first position (FIG. 11) to the second position (FIG. 12) causes the feet 26, which can extend in substantially opposite directions, to move away from each other. The opening 32 of the implant 28 can have a diameter greater than the sum of the diameters of the feet 26 of the moveable elements 20 and less than the sum of the diameters of the feet 26 and the distal end 16, whereby the implant 28 is fixed at the distal end, when the legs and distal end extend through the opening and the moveable elements are in the second position.

With the feet 26 close to one another, they can fit through the opening 32 in the implant 28. After the legs 21 are positioned within the opening 32, the elements 20 are retracted as shown in FIG. 12, whereby the distal end 16 causes displacement of the feet away from one another. The feet 26 prevent the implant 28 from separating from the distal end 16 thus removably attaching it to the distal end 16 of the shaft 12. The feet 26 contacting the inside surface of the implant 28 help transmit and distribute torque imparted from the distal end 16 to the implant 28. The implant 28 can be removed by reversing the order of attachment.

In other embodiments, major axes of the moveable elements 20 are positioned at an acute angle relative to one another, whereby movement of the moveable elements 20 from the first position to the second position causes the feet 26 to move away from one another.

Figure 13:
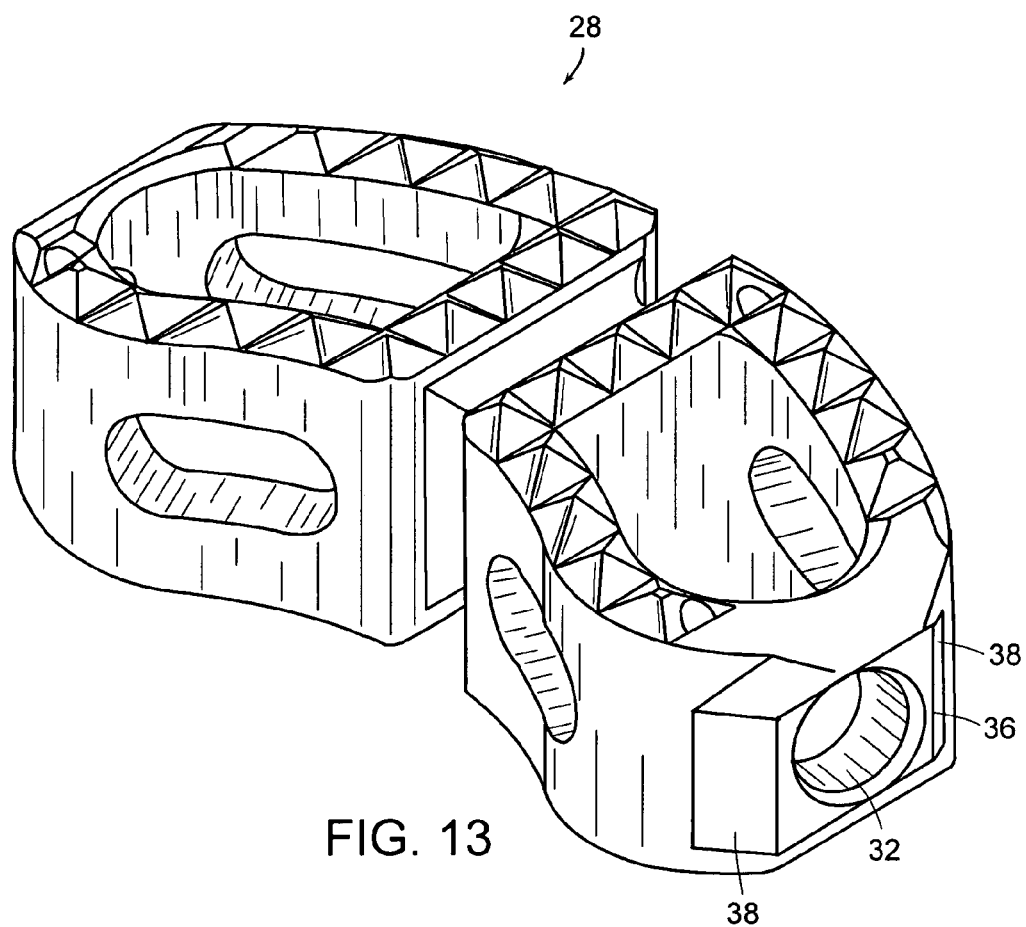
FIG. 13 is a perspective view of an implant provided in accordance with another embodiment of the present invention.

In further embodiments, the implant 28 and surface 25 can be shaped to prevent rotation of the implant when attached to the shaft 12. For example, as shown in FIG. 13, the implant 28 can be shaped to mate with the surface 25 along more than one surface. In one embodiment, the saddle 24 generally conforms to a portion of the surgical implant 28 and abuts the surgical implant when the moveable elements 20 and the distal end 16 extend through the opening 32 and the moveable elements are in the second position. The surgical implant 28 that conforms to the saddle 24 at least partially supports the position of the surgical implant relative to the shaft 12 when the moveable elements 20 and the distal end 16 extend through the opening 32 and the moveable ends are in the second position. The surgical implant 28 that conforms to the saddle 24 can include at least one flat surface. In other embodiments, the portion of the surgical implant 28 that conforms to the saddle 24 includes at least two flat surfaces that intersect. In one embodiment, a nut-like or bolt head-like structure 36 that can include at least two flat surfaces 38 can be provided on the implant 28 such that torque applied by a wrench-like structure provided on the distal end 16 is applied to the face of the implant 28 and not just through the opening 32 thus distributing loads over a larger surface preventing the implant 28 from failing at higher loads.

In other embodiments, the moveable elements 20 can be tapered to wedge into the opening 32 in the implant 28 to increase the holding force of the foot/feet 26 on the implant 28. In further embodiments, the foot/feet 26 can be tapered, which contact a curved inside surface of the implant 28 at two points.

While this invention has been particularly shown and described with references to preferred embodiments thereof, it will be understood by those skilled in the art that various changes in form and details may be made therein without departing from the scope of the invention encompassed by the appended claims.

What is claimed is:

1. A surgical device, the device comprising:
 a) a shaft having a proximal end and a distal end, the shaft defining a conduit;
 b) at least one moveable element, the element including a leg extending through the conduit and a foot at an end of the leg proximal to the distal end of the shaft, wherein the element is moveable relative to the shaft between a first position, in which the foot extends beyond the distal end, and a second, position, in which the foot is substantially adjacent to the distal end; and
 c) a surgical implant, the surgical implant defining an opening and wherein the foot diameter is smaller than a diameter of the opening, whereby the foot can be directed through the opening when the element is in the first position, and whereby the surgical implant is fixed at the distal end when the leg and distal end extend through the opening and the moveable element is in the second position.

2. A surgical device, the device comprising:
 a) a shaft having a proximal end and a distal end, the shaft defining a conduit; and
 b) at least two moveable elements, the elements each including a leg extending through the conduit and a foot at an end of the leg proximal to the distal end of the shaft, the element moveable relative to the shaft between a first position, wherein the foot extends beyond the distal end, and a second position, wherein the foot is substantially adjacent to the distal end; and
 c) a surgical implant, the surgical implant defining an opening, the opening of the surgical implant having a diameter greater than a sum of diameters of the feet of the moveable elements and less than the sum of the diameters of the feet of the elements and a diameter of the distal end of the shaft at a cross section of the feet and the distal end when the elements are in the second position, whereby the feet can be directed through the opening when the elements are in the first position, and whereby the surgical implant is fixed at the distal end when the legs and distal end extend through the opening and the moveable elements are in the second position.

3. The device of claim 2, wherein the moveable elements are on opposite sides of the distal end, whereby the feet of the moveable elements extend in substantially opposite directions from the distal end when the moveable elements are in the second position.

4. The device of claim 3, wherein major axes of the moveable elements are positioned at an acute angle relative to each other, whereby movement of the moveable elements from the first position to the second position causes the feet of the moveable elements to move away from each other.

5. The device of claim 4, wherein the moveable elements are arcuate, whereby movement of the elements from the first position to the second position distends the legs, thereby causing the feet to move away from each other.

6. The device of claim 2, further including a saddle located between the proximal and distal ends of the shaft.

7. The device of claim 6, wherein the saddle generally conforms to a portion of the surgical implant and abuts the surgical implant when the moveable elements and the distal end extend through the opening and said moveable elements are in the second position.

8. The device of claim 7, wherein the portion of the surgical implant that conforms to the saddle at least partially supports the position of the surgical implant relative to the shaft when the moveable elements and the distal end extend through the opening and the moveable ends are in the second position.

9. The device of claim 8, when the portion of the surgical implant that conforms to the saddle includes at least one flat surface.

10. The device of claim 9, wherein the portion of the surgical implant that conforms to the saddle includes at least two flat surfaces that intersect.

11. The device of claim 10, wherein the surgical implant is a vertebral cage.

12. The device of claim 11, wherein the vertebral cage is elongate.

13. The device of claim 12, wherein the opening is at an end of said elongate vertebral cage.

14. The device of claim 13, wherein the vertebral cage is generally arcuate.

15. The device of claim 1, wherein the foot is tapered.

16. The device of claim 1 wherein the distal end of the shaft is a projection and wherein the foot of the moveable element extends beyond the projection in the first position and the foot is substantially adjacent to the projection in the second position.

17. The device of claim 1 further including: a saddle located between the proximal and distal ends of the shaft.

18. A method for manipulating a surgical implant defining an opening, the method comprising:
  a) providing a shaft having a proximal end and a distal end, the shaft defining a conduit;
  b) providing at least one moveable element, the element including a leg extending through the conduit and a foot at an end of the leg proximal to
  the distal end of the shaft;
  c) inserting the foot through the implant opening when the movable element is in a first position, wherein the foot extends beyond the distal end; and
  d) moving the moveable element relative to the shaft between the first position and a second position, wherein the foot is substantially adjacent to the distal end and wherein the distal end extends through the implant opening, thereby removably fixing the surgical implant at the distal end.

19. The method of claim 18, further comprising removably attaching a surgical implant to the distal end, the surgical implant defining an opening, said opening having a diameter greater than a diameter of the foot, and less than the sum of the diameter of the foot and a diameter of the distal end of the shaft at a cross section of the foot and distal end of the shaft when the element is in the second position, whereby the foot can be directed through the opening when the element is in the first position, and whereby the surgical implant is fixed at. the distal end when the leg and distal end extend through the opening and the moveable element is in the second position.

20. The method of claim 17 wherein the distal end of the shaft includes a projection and wherein the moveable element is moved relative to the shaft from a first position, wherein the foot extends beyond the projection, to a second position, wherein the foot is substantially adjacent to the projection.

21. A method for manipulating a surgical implant, the method comprising:
  a) providing a shaft having a proximal end and a distal end, the shaft defining a conduit;
  b) providing at least two moveable elements, the elements each including a leg extending through the conduit and a foot at an end of the leg proximal to the distal end of the shaft; and
  c) moving each moveable element relative to the shaft between a first position, wherein the foot extends beyond the distal end, and a second position, wherein the foot is substantially adjacent to the distal end; thereby removably attaching the surgical implant to the distal end, the surgical implant defining an opening, the opening having a diameter greater than a sum of the diameters of the feet of the moveable elements and less than the sum of the diameters of the feet and a diameter of the distal end of the shaft at a cross section of the feet and distal end of the shaft when the elements are in the second position, wherein the feet can be directed through the opening when the elements are in the first position, whereby the surgical implant is fixed at the distal end when the legs and distal end extend through the opening and the moveable elements are in the second position.

22. A method for surgically implanting an intervertebral support, comprising the steps:
  a) inserting a moveable element into an opening defined by an intervertebral support, the moveable element having a leg and a foot at an end of the leg, and the opening having a diameter greater than a diameter of the foot and less than that of the foot and a distal end of a conduit-defining shaft through which the leg of the moveable element extends;
  b) moving the moveable element relative to the shaft from a first position, wherein the foot extends beyond the distal end, to a second position, wherein the foot is substantially adjacent to the distal end, whereby the distal end enters the opening of the intervertebral support and the foot is essentially adjacent to the distal end, thereby causing the intervertebral support to be fixed to the distal end;
  c) inserting the intervertebral support between two vertebrae of a patient;
  d) moving the moveable element from the second position to the first position, thereby releasing the intervertebral support from the shaft; and
  e) withdrawing the moveable element from the opening of the intervertebral support.

23. A device comprising:
  a) a shaft having a proximal end and a distal end, the shaft defining a conduit, wherein the distal end of the shaft defines a projection;
  b) at least one moveable element, the element including a leg extending through the conduit and a foot at an end of the leg proximal to the distal end of the shaft, the element moveable relative to the shaft between a first position, wherein the foot beyond the projection, and a second position, wherein the foot is substantially adjacent to the projection; and
  c) a surgical implant, the surgical implant defining an opening, said opening having a diameter greater than a diameter of the foot, and less than the sum of the diameter of the foot and a diameter of the projection at a cross section of the foot and the projection when the element is in the second position, whereby the foot can be directed through the opening when the element is in the first position, and whereby the surgical implant is fixed at the distal end when the leg and the projection extend through the opening and the moveable element is in the second position.

24. A method for manipulating a surgical implant, the method comprising:
   a) providing a shaft having a proximal end and a distal end, the shaft defining a conduit and wherein the distal end of the shaft includes a projection;
   b) providing at least one moveable element, the element including a leg extending through the conduit and a foot at an end of the leg proximal to the distal end of the shaft;
   c) moving the moveable element relative to the shaft between a first position, wherein the foot extends beyond the projection, and a second position, wherein the foot is substantially adjacent to the projection; thereby removably attaching the surgical implant to the distal end, the surgical implant defining an opening, said opening having a diameter greater than a diameter of the foot, and less than the sum of the diameter of the foot and a diameter of the projection at a cross section of the foot and the projection when the element is in the second position, whereby the foot can be directed through the opening when the element is in the first position, and whereby the surgical implant is fixed at the distal end when the leg and the projection extend through the opening and the moveable element is in the second position.

* * * * *